(12) United States Patent
McCarty, III

(10) Patent No.: US 10,085,736 B2
(45) Date of Patent: Oct. 2, 2018

(54) HOLLOW BODY ANCHOR

(71) Applicant: L. Pearce McCarty, III, Orono, MN (US)

(72) Inventor: L. Pearce McCarty, III, Orono, MN (US)

( * ) Notice: Subject to any disclaimer, the term of this patent is extended or adjusted under 35 U.S.C. 154(b) by 291 days.

(21) Appl. No.: 14/701,821

(22) Filed: May 1, 2015

(65) Prior Publication Data
US 2016/0317140 A1 Nov. 3, 2016

(51) Int. Cl.
A61B 17/04 (2006.01)
A61B 17/16 (2006.01)

(52) U.S. Cl.
CPC ...... *A61B 17/0401* (2013.01); *A61B 17/1637* (2013.01); *A61B 2017/0403* (2013.01); *A61B 2017/044* (2013.01); *A61B 2017/0409* (2013.01); *A61B 2017/0412* (2013.01); *A61B 2017/0414* (2013.01)

(58) Field of Classification Search
CPC . A61B 17/0401; A61B 17/04; A61B 17/3468; A61B 2017/0409; A61B 2017/0414; A61B 2017/0403
See application file for complete search history.

(56) References Cited

U.S. PATENT DOCUMENTS

| | | | |
|---|---|---|---|
| 4,431,416 A | 2/1984 | Niznick | |
| 4,744,754 A | 5/1988 | Ross | |
| 4,960,381 A | 10/1990 | Niznick | |
| 5,046,513 A | 9/1991 | Gatturna et al. | |
| 5,141,520 A | 8/1992 | Goble et al. | |
| 5,258,016 A | 11/1993 | DiPoto et al. | |
| 5,472,452 A | 12/1995 | Trott | |
| 5,554,171 A | 9/1996 | Gatturna et al. | |
| 5,713,921 A | 2/1998 | Bonutti | |
| 5,814,070 A | 9/1998 | Borzone et al. | |
| 5,904,704 A | 5/1999 | Goble et al. | |
| 6,146,407 A | 11/2000 | Krebs | |
| 6,165,203 A | 12/2000 | Krebs | |
| 6,641,596 B1 | 11/2003 | Lizardi | |
| 6,641,597 B2 | 11/2003 | Burkhart et al. | |
| 6,652,563 B2 | 11/2003 | Dreyfuss | |
| 6,890,354 B2 | 5/2005 | Steiner et al. | |
| 6,908,465 B2 | 6/2005 | von Hoffmann et al. | |
| 7,226,469 B2 | 6/2007 | Benavitz et al. | |
| 7,828,820 B2 | 11/2010 | Stone et al. | |

(Continued)

FOREIGN PATENT DOCUMENTS

| | | |
|---|---|---|
| EP | 0412845 | 12/1993 |
| EP | 0686373 | 12/1995 |
| EP | 2574284 | 4/2013 |

OTHER PUBLICATIONS

Notification of Transmittal of the International Search Report and the Written Opinion of the International Searching Authority, or the Declaration, dated Jul. 29, 2016.

*Primary Examiner* — Victor Nguyen
(74) *Attorney, Agent, or Firm* — Fish & Richardson P.C.

(57) ABSTRACT

Attachment of sutures to bone is achieved by forming a recess in the bone having a cylindrical channel surrounding a bone core and then inserting a hollow anchor body into the recess and over the bone core. Suture material is attached using openings in the anchor body and the suture material may be pinched between the inside and outside surfaces of the anchor body and the bone material.

20 Claims, 16 Drawing Sheets

(56) References Cited

U.S. PATENT DOCUMENTS

| | | |
|---|---|---|
| 8,137,381 B2 | 3/2012 | Foerster et al. |
| 8,403,957 B2 | 3/2013 | Martinek et al. |
| 8,460,340 B2 * | 6/2013 | Sojka ................ A61B 17/0401 606/230 |
| 8,512,378 B2 | 8/2013 | Green et al. |
| 8,632,568 B2 | 1/2014 | Miller et al. |
| 8,709,040 B2 | 4/2014 | Anderhub et al. |
| 8,764,798 B2 | 7/2014 | Housman |
| 8,821,541 B2 | 9/2014 | Dreyfuss et al. |
| 2006/0041261 A1 | 2/2006 | Osypka |
| 2007/0005068 A1 | 1/2007 | Sklar |
| 2007/0213730 A1 | 9/2007 | Martinek et al. |
| 2009/0088798 A1 * | 4/2009 | Snyder ............... A61B 17/0401 606/232 |
| 2009/0149883 A1 | 6/2009 | Brunsvold |
| 2010/0121348 A1 | 5/2010 | Van der Burg |
| 2012/0078298 A1 | 3/2012 | Sklar |
| 2013/0103080 A1 | 4/2013 | Hernandez |

* cited by examiner

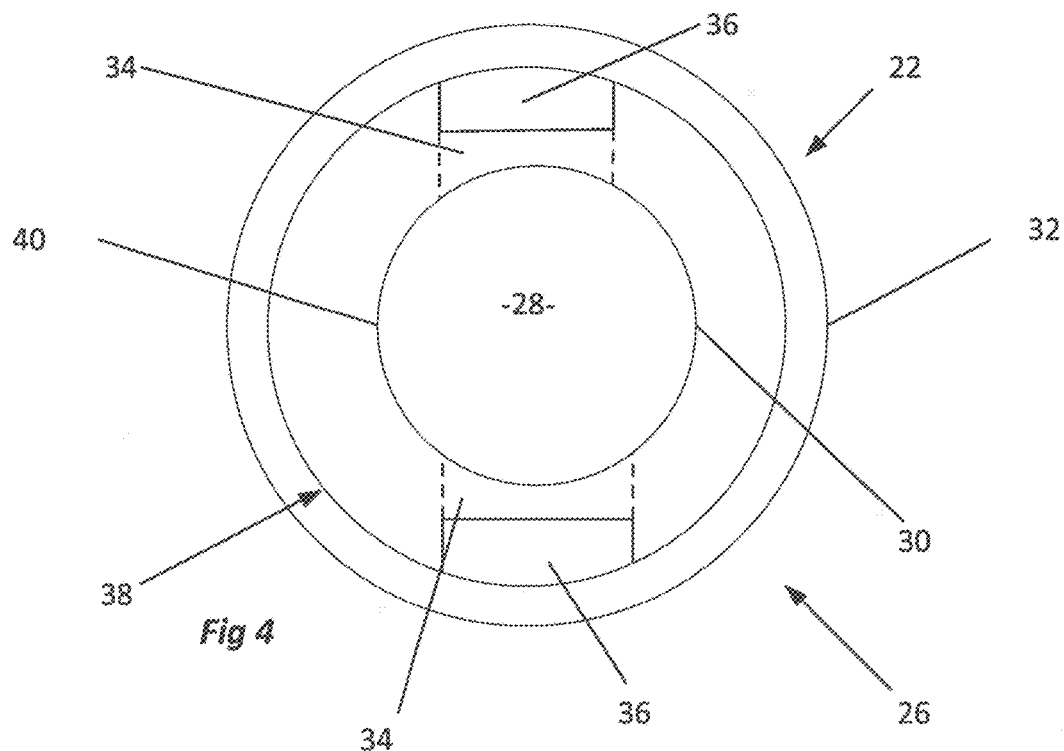
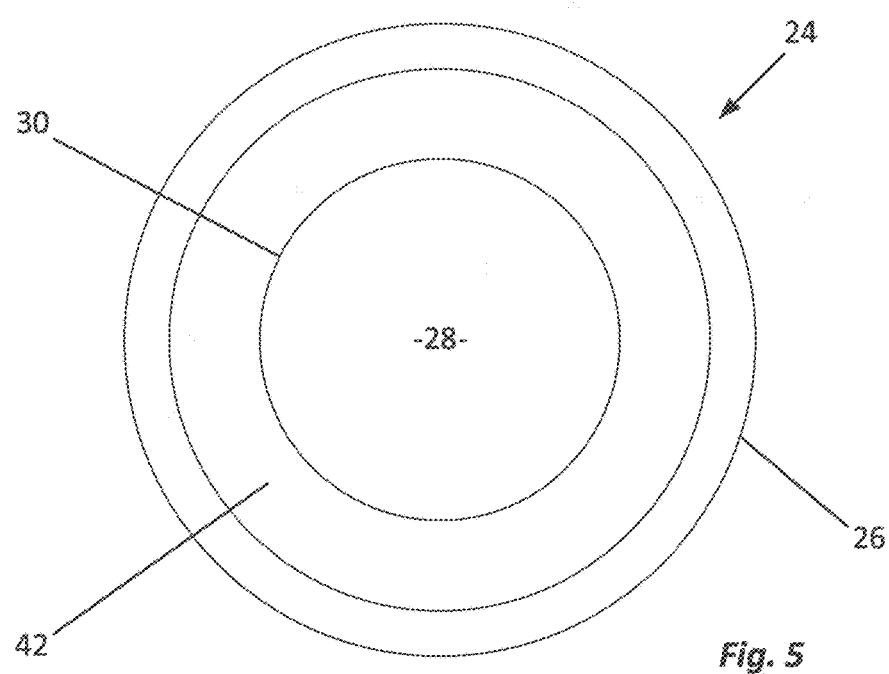

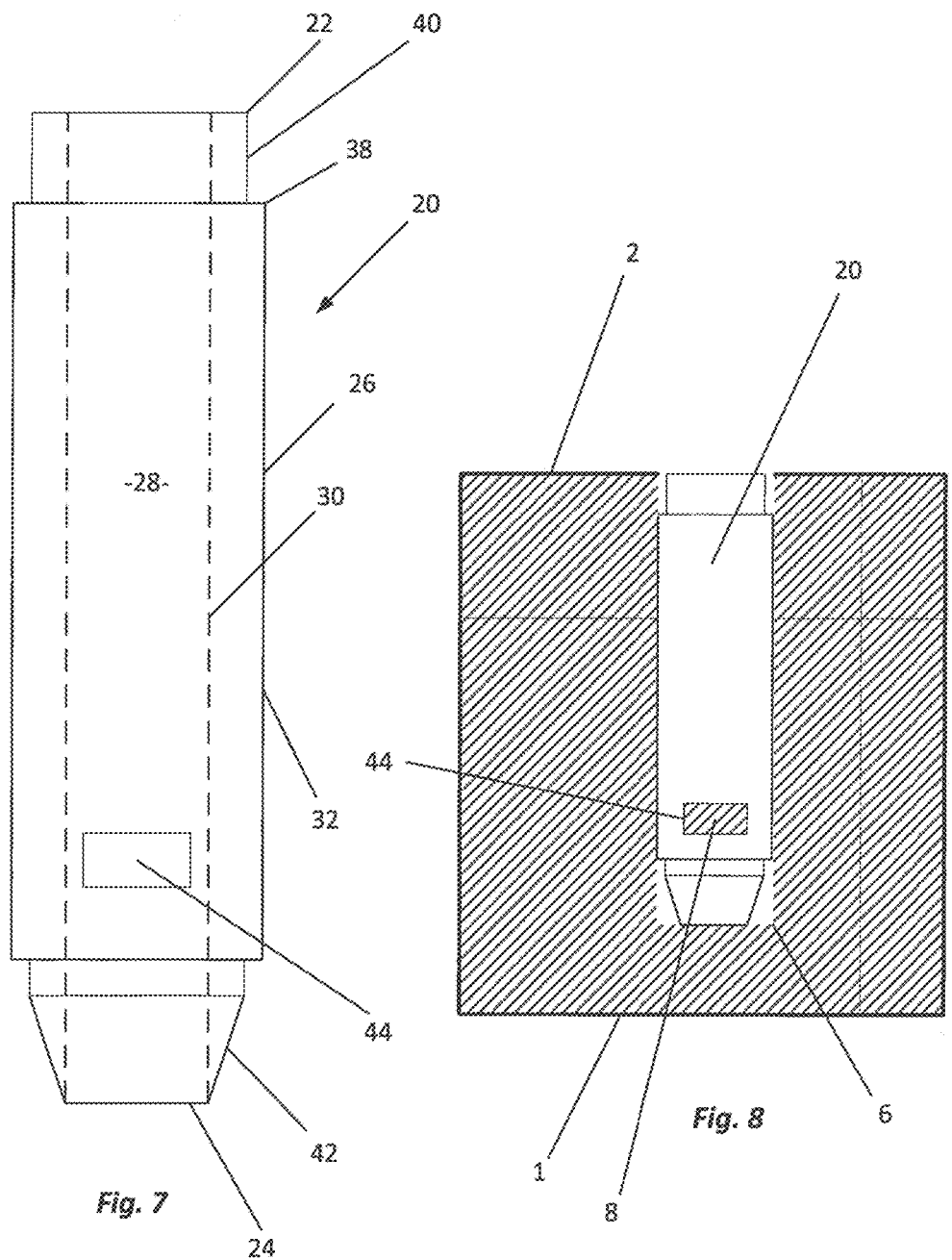

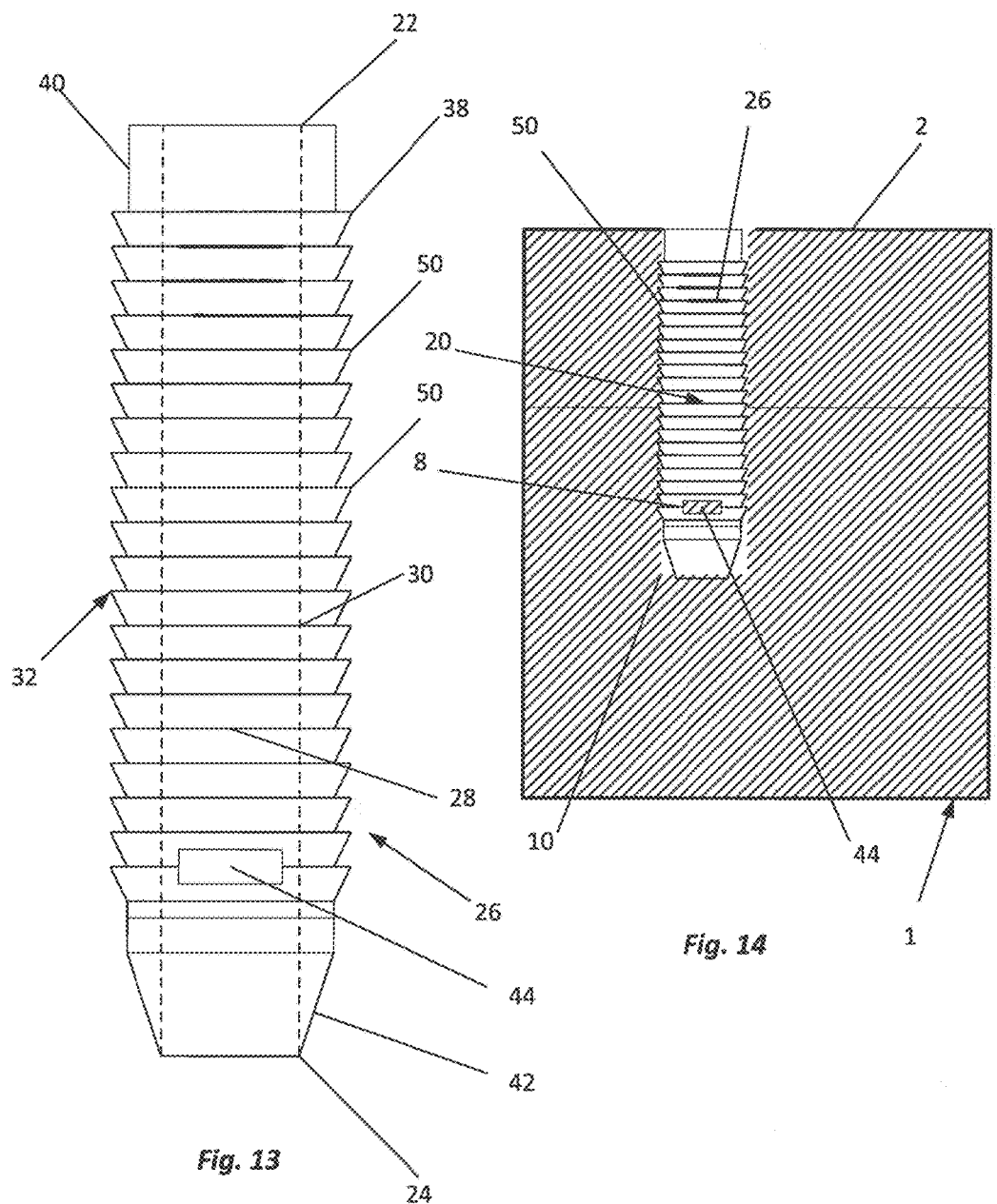

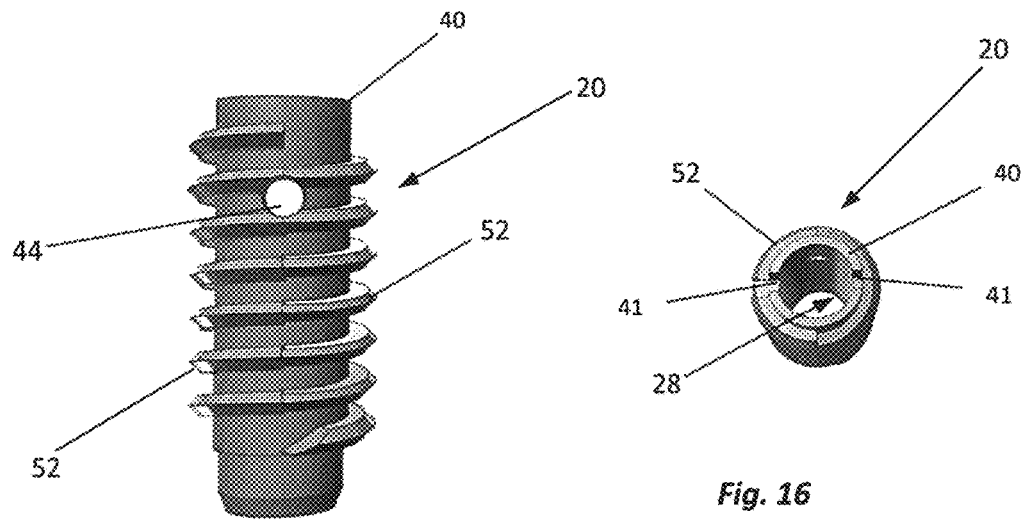
Fig. 15
Fig. 16
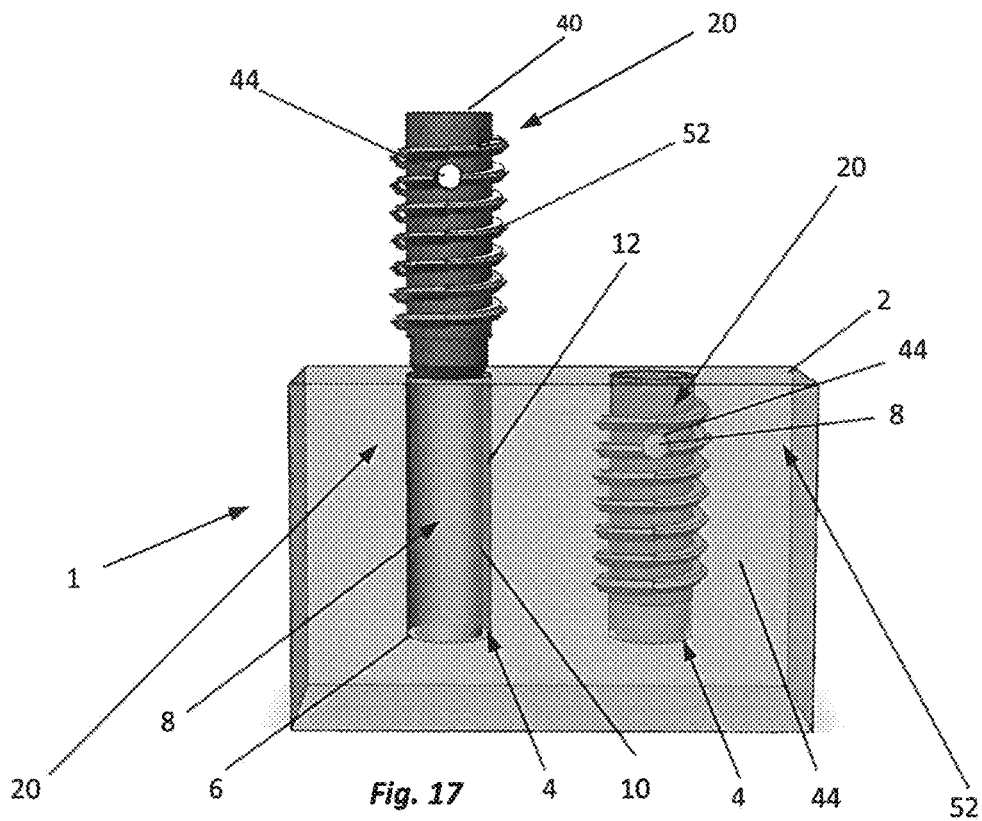
Fig. 17

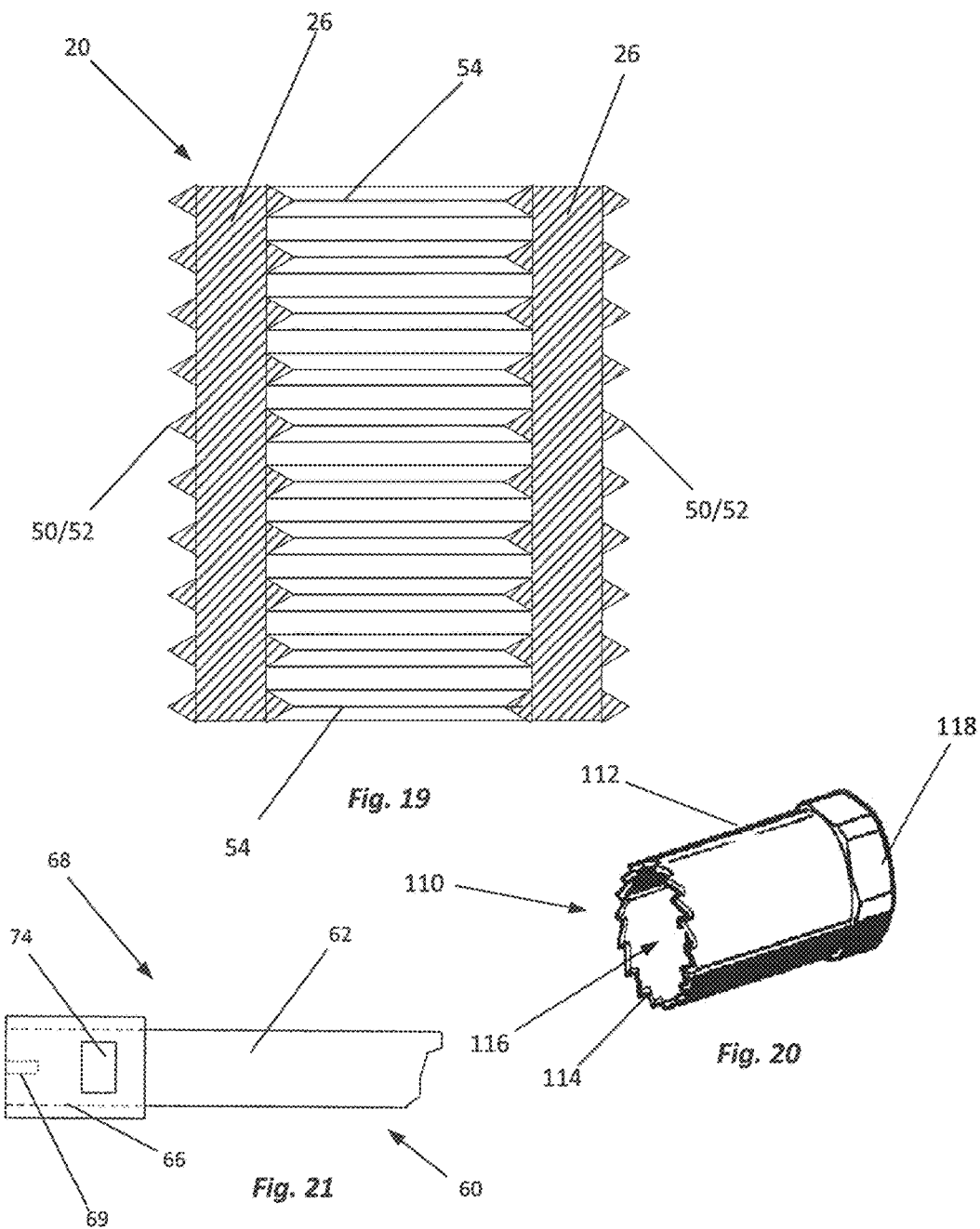

HOLLOW BODY ANCHOR

CROSS-REFERENCED TO RELATED APPLICATIONS

Not applicable.

STATEMENT REGARDING FEDERALLY SPONSORED RESEARCH OR DEVELOPMENT

Not applicable.

BACKGROUND OF THE INVENTION

I. Field of the Invention

The present invention relates to medical implants. More particularly, this invention relates to suture anchors used to attach soft tissue to bone.

II. Related Art

Surgeons have employed various types of suture anchors for decades for a variety of surgical applications. Suture anchors provide a surgeon with a means for attaching two pieces of tissue together so that they may heal. The tissues typically are tendon, ligament, or bone.

Prior to the development of suture anchors, surgeons would typically pass the suture material directly through bone utilizing sharp, trocar-tipped needles. Clamps or other similar instruments were sometimes used instead of sutures. In either case, a rather large surgical exposure was required resulting in increased surgical morbidity to the patient and longer healing times. The advent of suture anchors allowed the refinement of a variety of surgical procedures. Rather than using a conventional, open approach requiring a large incision, the use of suture anchors permitted the surgeon to employ a minimally invasive arthroscopic approach leading to less surgical morbidity and potentially faster healing rates for patients.

Suture anchors typically comprise two components—the body of the anchor and a suture material to be anchored to the bone. The body of the anchor can be made of a variety of different materials that are biocompatible, easily sterilized and strong enough to withstand the forces that may be exerted on the anchor. Such materials include, without limitation, titanium, alloys of stainless steel, polyether-ether ketone (PEEK), poly-1-lactic acid, and other biocompatible materials. An example of a material used to form the sutures is a polyester braid. The suture material is used to join tissue to the anchor body and the anchor body couples the suture material to a bone, providing an "anchor point" to the bone.

Prior art suture anchors typically have one of several designs that permit the body of the suture anchor to be secured to the bone. Most of these designs incorporate a solid body with exterior threads or ridges. When the anchor is a solid body incorporating exterior threads, a pilot hole is typically drilled into the bone and then the anchor body is screwed into the pilot hole and the threads prevent the anchor body from pulling out of the bone. Similarly, when a solid anchor body having ridges is employed, a pilot hole is drilled and the anchor body is impacted into the bone such that the ridges prevent the anchor body from being pulled out. Some anchor bodies are designed to expand such that the entire body or an element of the body expands as the anchor body is driven into the bone to prevent the anchor body from being pulled out of the bone.

Commercial suture anchors may come preloaded with the suture material. Alternatively, loading the suture anchor with the suture material may be performed by the surgeon. When the suture anchor comes preloaded, the anchor body is typically placed into the bone at an anchor point and then the suture material is passed through or around a piece of tissue to be joined to the bone at the anchor point. The sutures are then tied, securing the piece of tissue to the anchor body which has already been placed in the bone at the anchor point. When the suture anchors are not preloaded with suture material, free sutures are typically passed by the surgeon through or around a piece of tissue that the surgeon wishes to anchor to the bone. The sutures are then fed through the anchor body and the anchor body is impacted into the bone pulling the tissue down to the anchor point.

The sutures are secured within the anchor body in various manners. In some situations, this fixation is made without tying knots and the anchor is referred to as a "knotless" anchor. When knotless anchors are used, an internal locking mechanism is provided such that the sutures are locked to the anchor body via the locking mechanism. The locking mechanism typically operates by pinching the sutures. In other cases, the sutures are extended between the bone and the external surfaces of the anchor body such that when the anchor body is inserted into the bone at the anchor point, the sutures are pinched between the bone and the anchor body.

While a number of surgical procedures have been successfully performed using prior art suture anchors, surgeons sometimes encounter difficulties implanting such suture anchors arthroscopically. Thus, to complete the surgical procedure, a large surgical exposure is created. This serves to increase trauma, pain, risk of nerve and tissue damage, and healing time. Further, during recovery and before healing is complete, excessive forces may be applied to the sutures and anchor body by the tendon, ligament or bone which can result in the suture anchor dislodging from the bone or the sutures dislodging from the anchor body. Additional surgical repair is required should such dislodging occur. Still further, upon removal or dislodging of currently existing suture anchors, a cylindrical defect is left in the host bone. Such a defect may serve as an impediment to placement of new anchors for revision surgery. Additionally, many "knotless" suture anchors have complex internal locking mechanisms that may present technical difficulties for the surgeon performing the procedure during actuation of the locking mechanism. As such, there is a real need for an improved suture anchor which can be readily and easily implanted arthroscopically, is simple to use, will be securely bound to the bone, and at the same time will securely couple the sutures to the anchor body and bone.

SUMMARY OF THE INVENTION

An improved suture anchor design provides an anchor body having an open top, an open bottom, and a generally cylindrical wall extending between the open top to the open bottom. The cylindrical wall defines inner engagement surfaces surrounding a channel extending from the open top to the open bottom and an outer engagement surface. Use of the suture anchor incorporating these features permits the anchor body to be used with a uniquely shaped recess prepared in the bone. Such a recess extends inwardly from an exposed surface of the bone at the desired point of attachment (i.e., the anchor point) and comprises a cylindrical hole extending inwardly from the exposed surface to a base. The cylindrical hole surrounds a bone core extending from the base toward the exposed surface of the bone.

Such a recess has at least two engagement surfaces, specifically an outer bone surface at the outside of the cylindrical wall and also an inner bone surface, i.e., surface of the bone core. The anchor body is adapted to permit the cylindrical wall (or at least a portion thereof) to be inserted into the cylindrical hole of the recess such that the bone core resides in the channel of the anchor body. As such, the outer engagement surface of the anchor body engages the outer bone surface of the recess and the inner engagement surface of the anchor body engages the bone core. This serves to substantially increase the surface area of the bone engaged by the anchor body for increased holding power. This also results in substantially less bone material being removed when forming the recess than is the case with traditional solid body bone anchors.

In some embodiments the anchor body may have vents through the walls of the anchor to permit vascular flow and bone growth between the bone along the external engagement surface of the anchor and the central bone core against the internal engagement surface. Bone growth through these vents would serve to further reinforce anchor fixation to bone, preventing dislodgement.

To further increase the holding power of the bone anchor, ridges or threads may be provided on either the outer engagement surface of the anchor body, the inner engagement surface of the anchor body or both the inner and outer engagement surfaces of the anchor body. Various structures may be coupled to the anchor body to permit preloading of the anchor body with suture material.

More specifically, in one embodiment the anchor body may be designed to be impacted directly into the recipient recess with external ridges present oriented in such a manner as to achieve a friction fit between the external engagement surface of the anchor and the surrounding bone, thereby resisting extraction or pullout of the anchor body. In other embodiments, internal ridges may also be added to the internal surface of the device to provide a similar friction fit between the internal engagement surface of the anchor and the central core of bone. The anchor body may alternatively, in other embodiments, be designed to be screwed into place with threads present on the external engagement surface of the anchor that will engage the surrounding bone. Internal threads may also be added to the internal engagement surface of the device to provide a similar threaded purchase against the central core of bone. The pitch of the internal threads would match that of the external threads to permit the anchor body to advance in the same fashion with engagement of both external and internal threads.

Various structures may be coupled to the anchor body to permit loading of the anchor body with suture material. For example, with a threaded design in which threads are fashioned along the external surface of the anchor body, permitting the anchor to be screwed into the recipient cylindrical socket, a short, hollow, cylindrical cap may be loaded with suture and positioned at the distal tip of the anchor such that in the process of screwing the anchor body into place the cap is driven into and secured in the bone at the distal end of the anchor body.

Using the hollow anchor body described above with a hollow center that embraces a bone core is particularly advantageous when employing a knotless suturing technique. The suture material is held more securely to the anchor body and the bone because the suture material is not only captured between the outer engagement surface of the anchor body and the outer bone surface, but is also captured between the inner engagement surface of the anchor body and the central bone core. These two areas of engagement may be provided by creating a loop of suture material which is adapted to reside between the outer engagement surface of the anchor body and the outer bone surface with other portions of the suture material extend into and through the channel of the suture anchor such that these portion is of the suture material reside between the inner engagement surface of the anchor body and bone core. The suture material may pass through the open bottom of the anchor body. Alternatively, an orifice or passageway may be provided through the cylindrical wall between the inner engagement surface and the outer engagement surface adjacent the open bottom of the anchor body. Such an orifice or passageway reduces the risk that the suture material will be cut by the bottom of the anchor body as it is driven into the bone recess formed at the anchor point. The suture material may also be passed through an orifice or passageway in a short, hollow, cylindrical cap that engages the distal tip of the anchor body in a manner as described above.

The suture anchor may be provided as part of a kit that also includes a tool for forming a recess in the bone at an anchor point of the type described above. For those embodiments of the anchor device possessing threads along the engagement surface(s), the kit may also include a tool for forming and tapping a recess in the bone at an anchor point of the type described above. The kit may also include an insertion tool for advancing the anchor body into the recess until the open bottom of the anchor body reaches the base of the recess with the bone cores residing within and extends up through the channel of the anchor body.

Alternatively, in some embodiments, the distal tip of the anchor body (or a distal cap associated therewith) may be reinforced with a sharpened ring of metal alloy that permits the anchor body to form its own recess as it is being impacted into the recipient bone, without the need for prior formation of the recess. In such embodiments, the anchor body would be considered "self-punching" as it would form its own recess.

The anchor body and insertion tool are, of course, adapted to permit the anchor body to be coupled to the insertion tool during the insertion process and then decoupled from each other to permit extraction of the insertion tool while leaving in place the anchor body and any sutures attached thereto. The insertion tool may include a channel that is in communication with the channel of the anchor body when the two are joined together. The insertion tool may also have a separate passageway extending from its channel out of a portion of the wall of the insertion tool. As such, suture material may be fed (i) in through the orifice in the wall of the anchor body, (ii) up through the channel of the anchor body, (iii) into the channel of the insertion tool, and then (iv) out through the passageway of the insertion tool such that, upon insertion of the anchor body, the suture material is pinched between not only the anchor body and the outer bone surface, but also between the anchor body and the bone core. A wire loop or loops may be provided to facilitate the passage of suture material through said passageways.

Other features and advantages of the present invention will become apparent from the following detailed description of the invention, which refers to the accompanying drawings.

BRIEF DESCRIPTION OF THE DRAWINGS

The foregoing features, objects and advantages of the invention will become apparent to those skilled in the art from the following detailed description and with reference to the following drawings in which like numerals and the several views refer to corresponding parts.

FIG. 4 is a top view of the anchor body of FIG. 3.

FIG. 5 is a bottom view of the anchor body of FIG. 3.

FIG. 7 is a side elevational view of a second embodiment of an anchor body.

FIG. 8 shows the anchor body of FIG. 7 implanted in a piece of bone at an anchor point, the bone being shown in cross-section.

FIG. 13 is a side elevational view of a fourth embodiment of an anchor body.

FIG. 14 shows the anchor body of FIG. 13 implanted in a section of bone at an anchor point, the bone being shown in cross-section.

FIG. 15 is side elevational view of a fifth embodiment of an anchor body.

FIG. 16 is a top view of the anchor body shown in FIG. 15.

FIG. 17 shows the anchor body of FIG. 15 aligned with the recess of FIGS. 1 and 2 (left) and implanted in the recess (right).

FIG. 19 is a cross-section of a portion of the cylindrical wall of an anchor body having both external and internal threads or ridges.

FIG. 20 is a perspective view of a recess forming tool adapted to form a recess in a bone of the type shown in FIGS. 1 and 2.

FIG. 21 shows an anchor body insertion tool.

DETAILED DESCRIPTION

Figure 1:
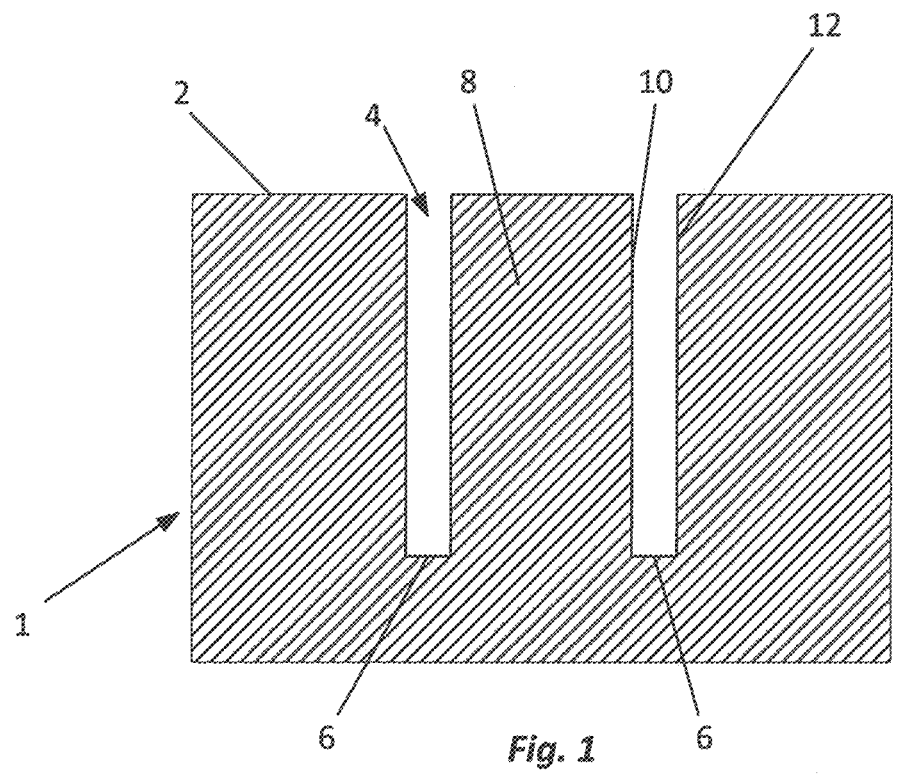
FIG. 1 is a cross-section of a piece of bone showing a recess formed therein at an anchor point.

In the following detailed description, references made to various exemplary embodiments in which the invention may be practiced. These embodiments are described with sufficient detail to enable those skilled in the art to practice the invention, and it is understood that other embodiments may be employed, and that structural and other changes may be made without departing from the spirit or scope of the present invention.

This description of the preferred embodiment is intended to be read in connection with the accompanying drawings, which are to be considered part of the entire written description of this invention. In the description, relative terms such as "lower", "upper", "horizontal", "vertical", "above", "below", "up", "down", "top" and "bottom", "under", as well as derivatives thereof (e.g., "horizontally", "downwardly", "upwardly", "underside", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "joined", and "joining" are used interchangeably and refer to one structure or surface being secured to another structure or surface or integrally fabricated in one piece unless expressly described otherwise.

Figure 2:
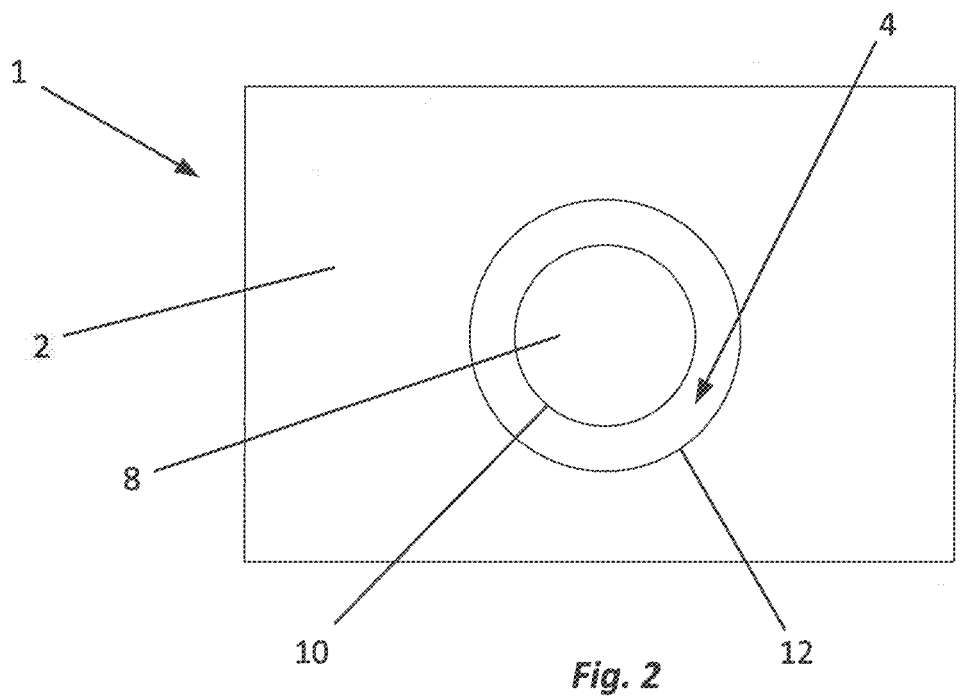
FIG. 2 is a top view of a piece of bone showing a recess form therein at an anchor point.

FIGS. 1 and 2 illustrate a recess that is formed at an anchor point in a section of bone when the various embodiments described below are employed. More specifically, these drawings show, in cross-section, a portion 1 of bone having an exposed surface 2. Formed into the bone 1 from the exposed surface 2 is a cylindrical hole 4 having a base 6. The cylindrical hole 4 surrounds a bone core 8. As such, the recess has an inner bone surface 10 and an outer bone surface 12. Such a recess may be forms using any of a variety of tools. An example of such a recess forming tool 110 is shown in FIG. 20. The recess forming tool 110 has a hollow cylindrical body 112 extending between a cutting edge 114 and a driving end 118. The cutting edge 114 may be serrated as shown or may be a single sharpened edge. The cutting edge surrounds an opening 116. The recess forming tool 110 may be employed as a punch or coupled to a rotary tool and used like a hole saw.

Figure 6:
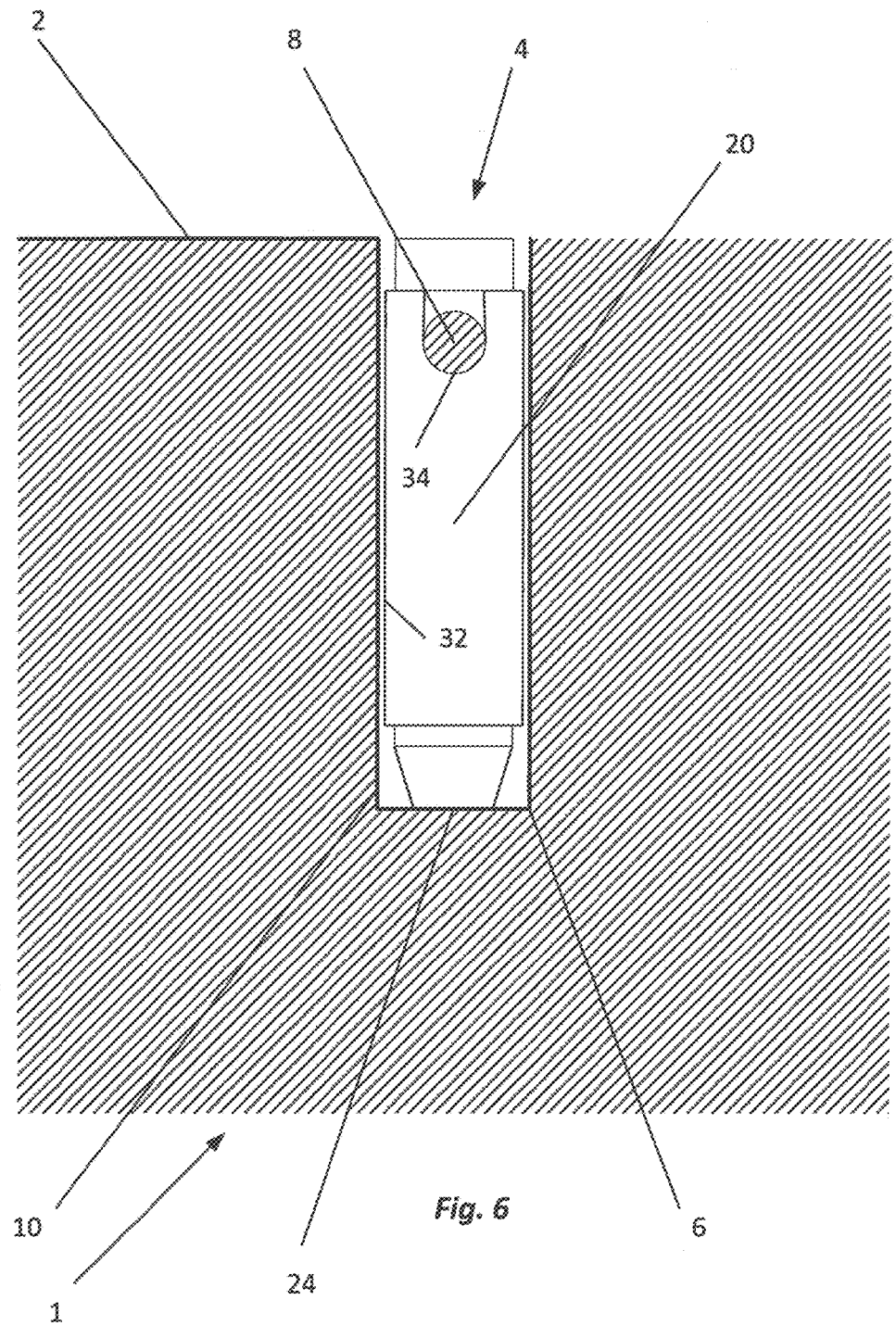
FIG. 6 shows the anchor body of FIG. 3 implanted in a piece of bone at an anchor point, the bone being shown in cross-section.

FIGS. 3-6 illustrate a first embodiment of an anchor body 20 which is designed to be inserted into the recess shown in FIGS. 1 and 2 as is best illustrated in FIG. 6. The anchor body 20 has an open top 22, an open bottom 24 and a generally cylindrical wall 26 which extends between the open top 22 and the open bottom 24. The cylindrical wall 26 includes a central channel 28 which extends from the open top 22 to the open bottom 24. The channel 28 defines an inner engagement surface 30. The outside of the cylindrical wall 26 defines and outer engagement surface 32.

The embodiment shown in FIGS. 3-6 also includes a pair of first orifices 34 which are axially aligned and extend through the cylindrical wall 26 between the inner engagement surface and the outer engagement surface. These first orifices 34 each provide an additional access pathway to the channel 28 of anchor 20. The cylindrical wall 26 has a recess 36 which extends upwardly from each of the first orifices 34. The fact that there are two such orifices 34 and two such recesses 36 is best illustrated in FIG. 4. The orifices 34 make it possible to pass suture material (not shown in FIGS. 3-6) through the cylindrical wall 26. Such suture material also extends up through the recesses 36 when the cylindrical suture anchor is positioned as shown in FIG. 6. The suture material may be formed into any suitable suture member. As used herein, "suture member" refers to any suture, any suture tape or other flexible, strong, elongate material which may be used interchangeably with either a traditional suture or suture tape.

Figure 3:
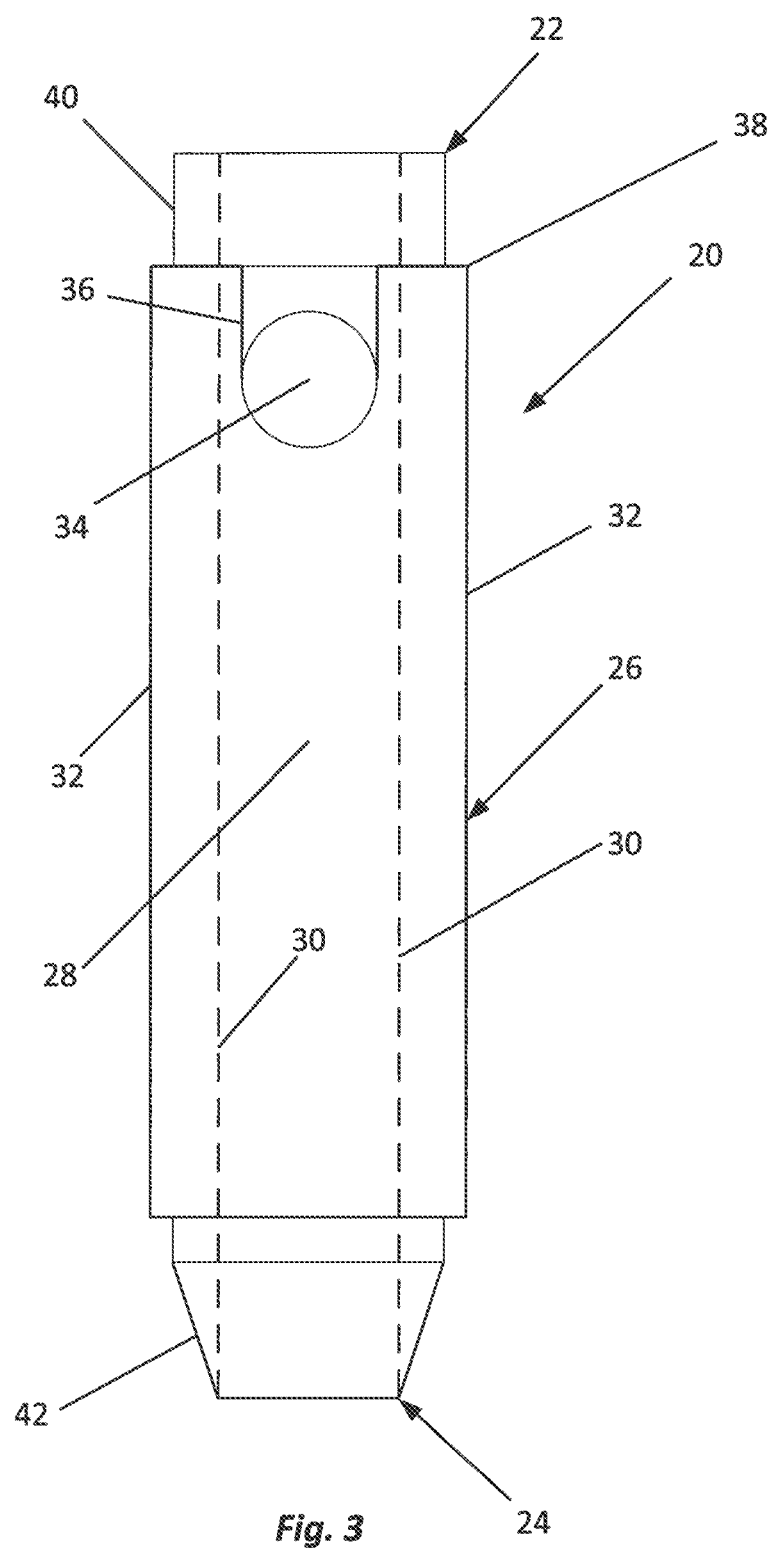
FIG. 3 is a side elevational view of a first embodiment of an anchor body.
Figures 22, 23:
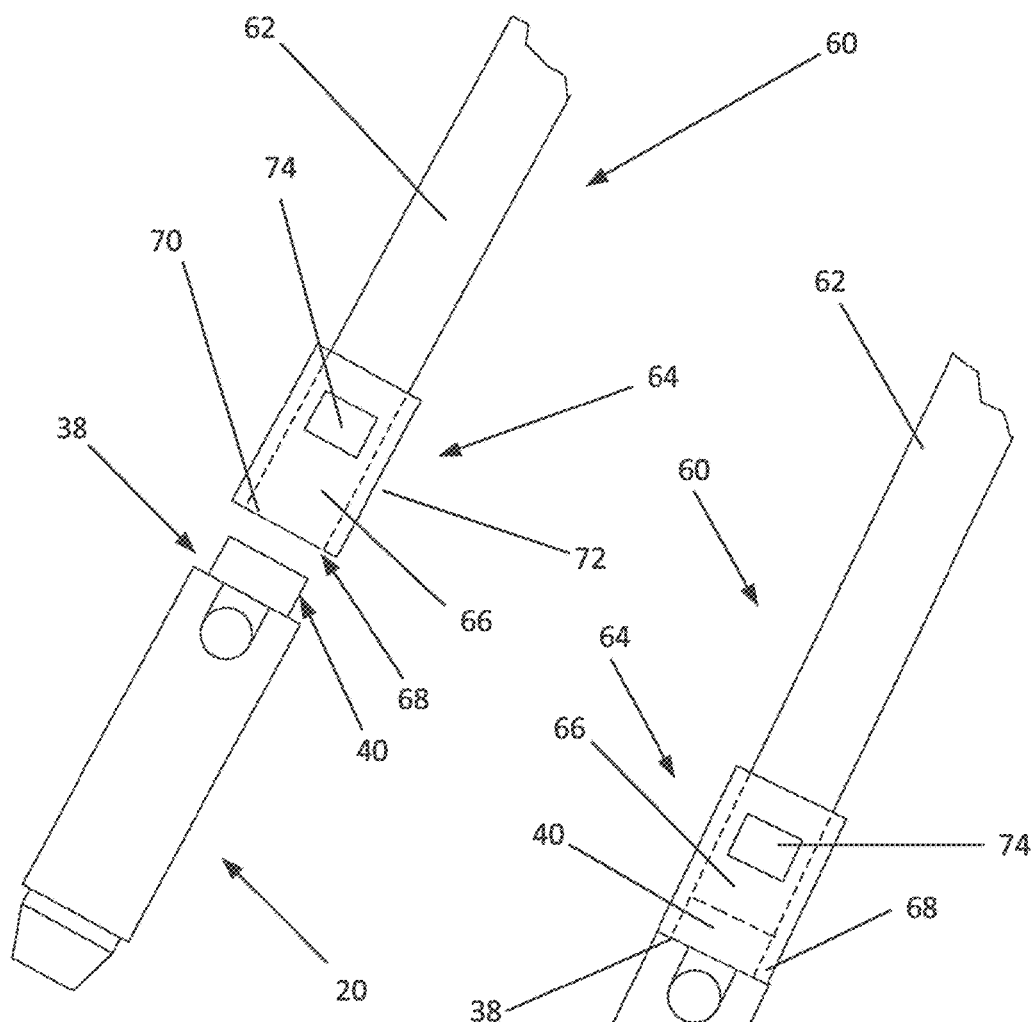
FIG. 22 shows and anchor body insertion tool and an anchor body.
FIG. 23 shows the anchor body insertion tool and anchor body of FIG. 22 joined together.

To make it easier to align and insert the anchor body 20 shown in FIG. 3, the bottom portion of the anchor body 20 has a tapered section 42. Further, the top portion of anchor body 20 includes a flange 38 surrounding a narrowed projecting portion 40. These are used to couple the anchor body 20 to an insertion tool 60 as illustrated in FIGS. 21 and 22 and discussed in greater detail below.

As illustrated in FIG. 6, the anchor body 20 is intended to be inserted within the cylindrical hole 4 such that the bone core 8 extends up through the channel 28 of suture anchor 20. A portion of the bone core 8 is visible through the first orifice 34.

FIG. 6 shows the open bottom 24 of the suture anchor 20 resting on the base 6 of the cylindrical hole 4. The open top 22 of the anchor body 20 is substantially flush with the exposed surface 2 of the bone 1. Those of ordinary skill in the art will recognize that in some applications it may be desirable to recess the anchor body 20 below the exposed surface 2 of the bone. In other surgical applications, it may be desirable to leave a portion of the suture anchor 20 exposed.

While sutures are not shown in FIGS. 3-6, one skilled in the art should understand that these sutures would pass through the aligned orifices 34 on the front and back of the anchor body 20 and then extend up through the recesses 36 which extend upwardly from these orifices 34 on the front and back of the anchor body 20. The sutures can then be used to attach a ligament, tendon or other structure to the bone. The anchor body 20 shown in FIGS. 3-6 may be preloaded with sutures to form the suture anchor.

FIGS. 7 and 8 show an alternative embodiment similar to that shown in FIGS. 7 and 8. In the embodiment of FIG. 7 and 8, the first orifice has been replaced an orifice 44 closer to the bottom of the anchor body 20. In FIG. 8, the bone core is visible through this orifice 44. While only one such orifice 44 is shown in the drawings, one skilled in the art will recognize that additional orifices may be provided. As will be discussed in greater detail below with reference to FIGS. 23 and 24, the arrangement shown in FIGS. 7 and 8 is well suited for a knotless suture application.

Figure 9:
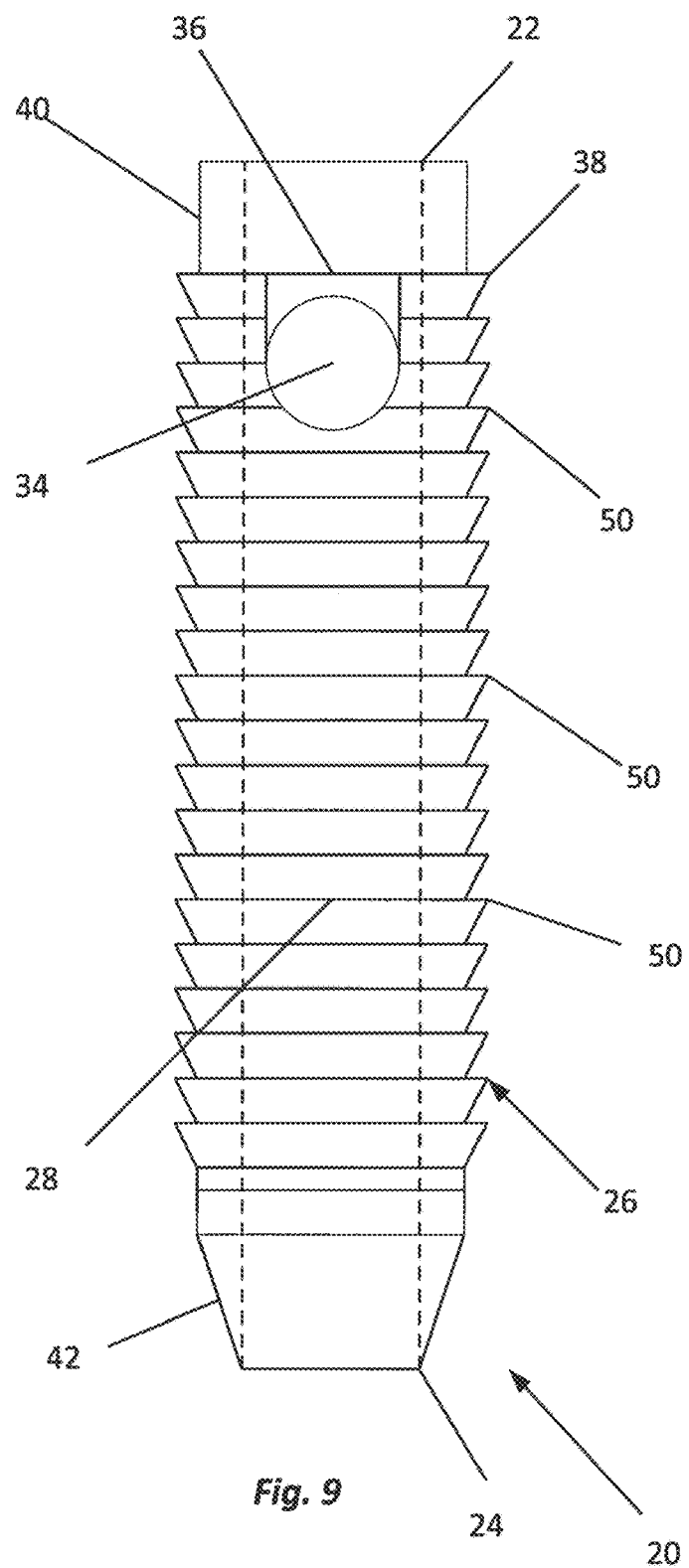
FIG. 9 is a side elevational view of a third embodiment of an anchor body.
Figure 10:
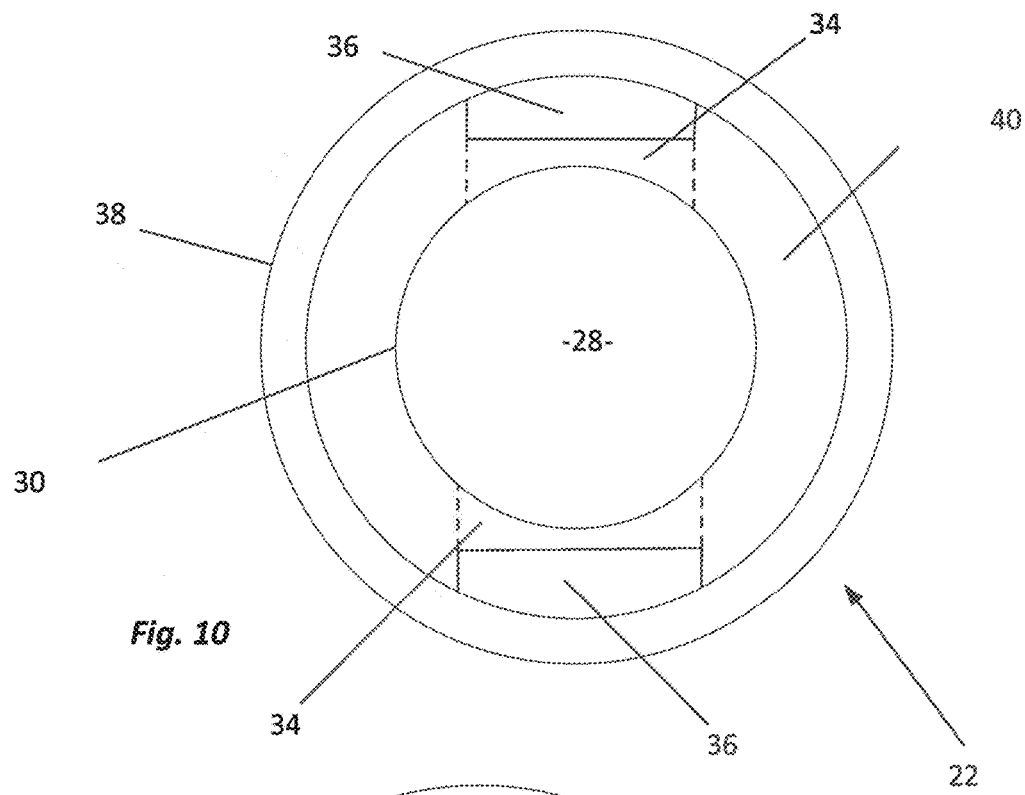
FIG. 10 is a top view of the anchor body of FIG. 9.
Figure 11:
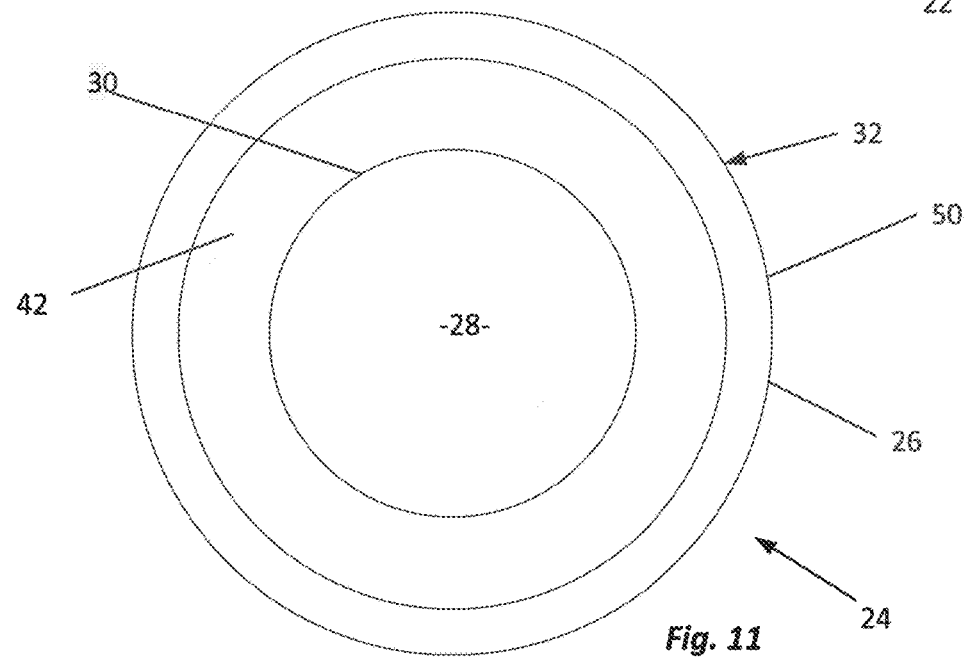
FIG. 11 is a bottom view of the anchor body of FIG. 9.
Figure 12:
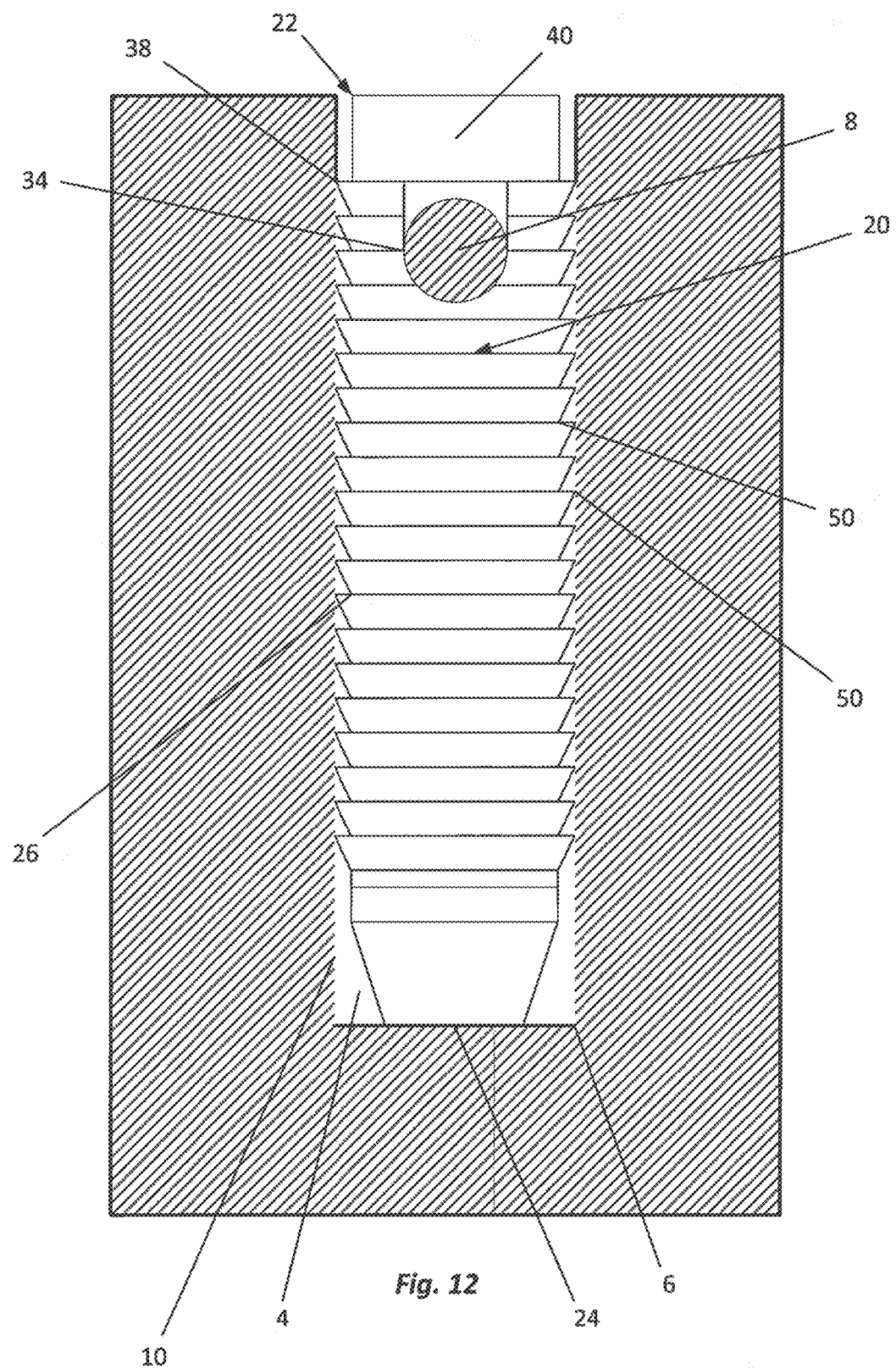
FIG. 12 shows the anchor body of FIG. 9 implanted in a section of bone at an anchor point, the section of bone being illustrated in cross-section.
Figure 26:
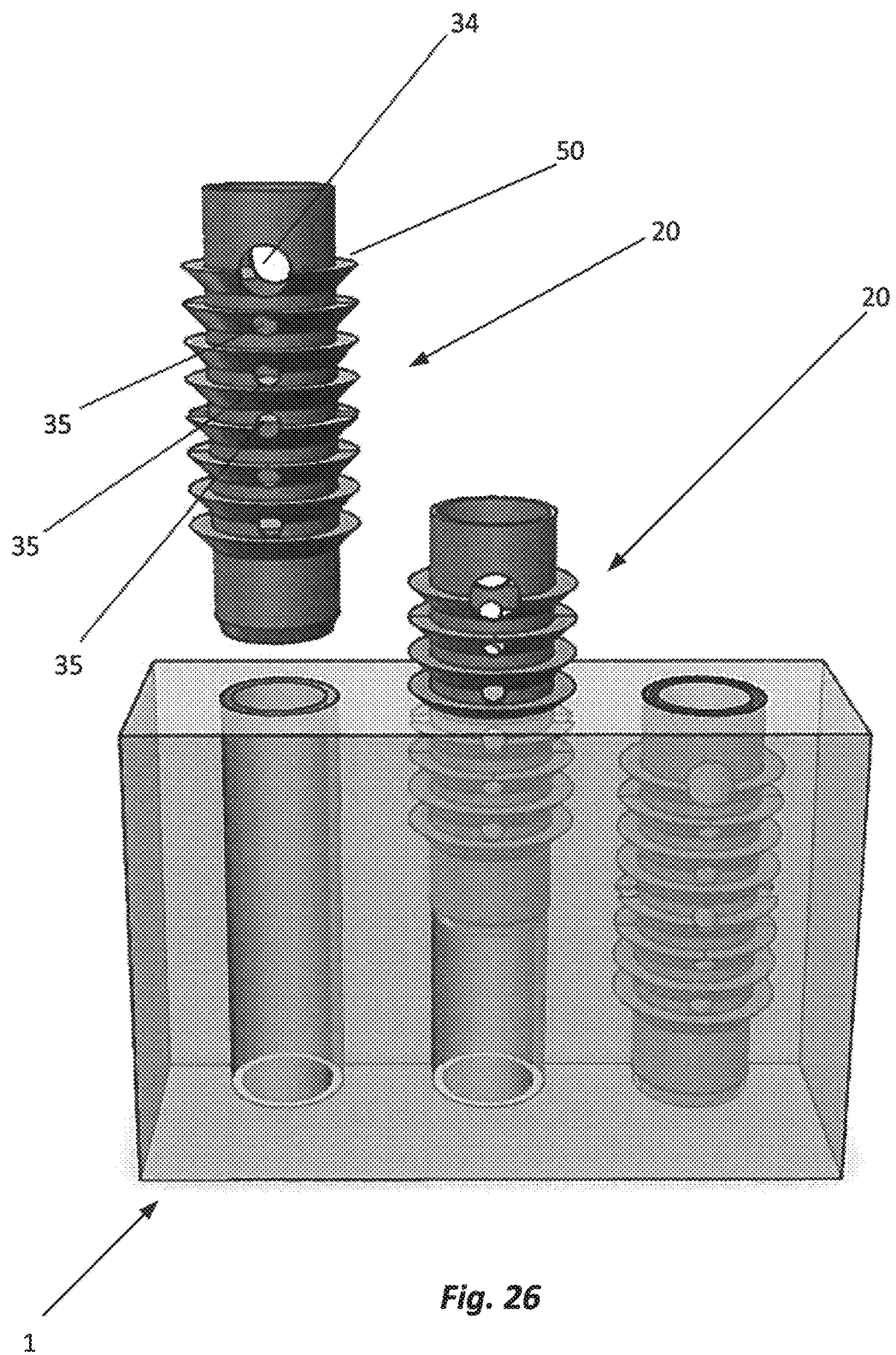
FIG. 26 shows a seventh embodiment of an anchor body aligned with the recess of FIGS. 1 and 2 (left), partially implanted (center), and fully implanted in the recess (right).

FIGS. 9-12 show an embodiment of anchor body 20 similar to that shown in FIGS. 3-6. In the embodiment of FIGS. 9-12, ridges 50 extend from the outer engagement surface of the cylindrical wall 26 of anchor body 20. These ridges 50 assist in binding the anchor body 20 to the bone. As best illustrated in FIG. 12, the ridges 50 engage the outer bone surface 12 to lock the anchor body 20 in place after it has been inserted into the cylindrical hole 4 and pushed down against the base 6 of the cylindrical hole 4. When the embodiment of FIGS. 9-12 is employed, the anchor body 20 is impacted into position such that the bone core 8 extends through the open bottom 24 and channel 28. A portion of the bone core 8 is visible through orifice 34 in FIG. 12. A similar embodiment to that shown in FIGS. 9 and 12 is shown in FIG. 26. In this and other embodiments the anchor body 20 may be provided with vents 35 through the wall of the anchor body 20 to permit vascular flow and bone growth between inner bone surface 10 and the outer bone surface 12, i.e., the bone of the bone core 8 along the internal engagement surface of the anchor body 20 and the bone against the external engagement surface of the anchor body 20. Bone growth through these vents serves to further reinforce anchor fixation to bone, preventing dislodgement.

FIGS. 13 and 14 show an embodiment similar to that shown in FIGS. 7 and 8. As illustrated in FIGS. 13 and 14, ridges 50 have added to the outer engagement surface 32 of the cylindrical wall 26. These ridges 50 are adapted to engage the outer bone surface 12 to secure the anchor body 20 within the cylindrical hole 4 formed in the bone 1 as shown in FIG. 14.

In lieu of ridges 50 of the embodiments illustrated in FIGS. 9-14, the cylindrical wall 26 of the anchor body 20 may be provided with exterior threads. Such threads 52 are illustrated in the embodiments shown in FIGS. 15-18. The threads 52 are self-tapping such that when the anchor body 20 is screwed into the end of the cylindrical hole 34, mating threads are formed in the bone itself which cooperate with the threads 52 to help capture the anchor body 20 in place within the cylindrical hole 4. In the embodiment shown in FIG. 18, the projecting portion 40 has a tool receiving notch 41 discussed below.

FIG. 19 shows an additional feature of the anchor body 20 which may be employed with any of the previously described embodiments. Specifically, the cylindrical wall 26 may be provided with both exterior ridges or threads 50/52 and interior threads or ridges 54. When two sets of threads are employed, both sets of threads are self-tapping. As such, when the anchor body 20 is screwed into the cylindrical hole 4, mating threads are formed in both the outer bone surface 12 and the inner bone surface 10 (i.e., the exterior of the bone core 8 to provide even more holding power. Of course, one skilled in the art should understand that in lieu of such interior and exterior threads, interior and exterior ridges may be provided to achieve similar holding power.

While anchor bodies of the type described above may be manufactured and packaged separately, it is also possible to provide to such anchor bodies as part of a kit. The kit may also include the suture material, a tool for forming the cylindrical hole 4 in the bone 1 while leaving the bone core 8 in place at the anchor point, and an insertion tool. The tool forming the hole can be a punch or drill designed to form the cylindrical hole 4 while leaving the bone core 8 in place.

Figure 24:
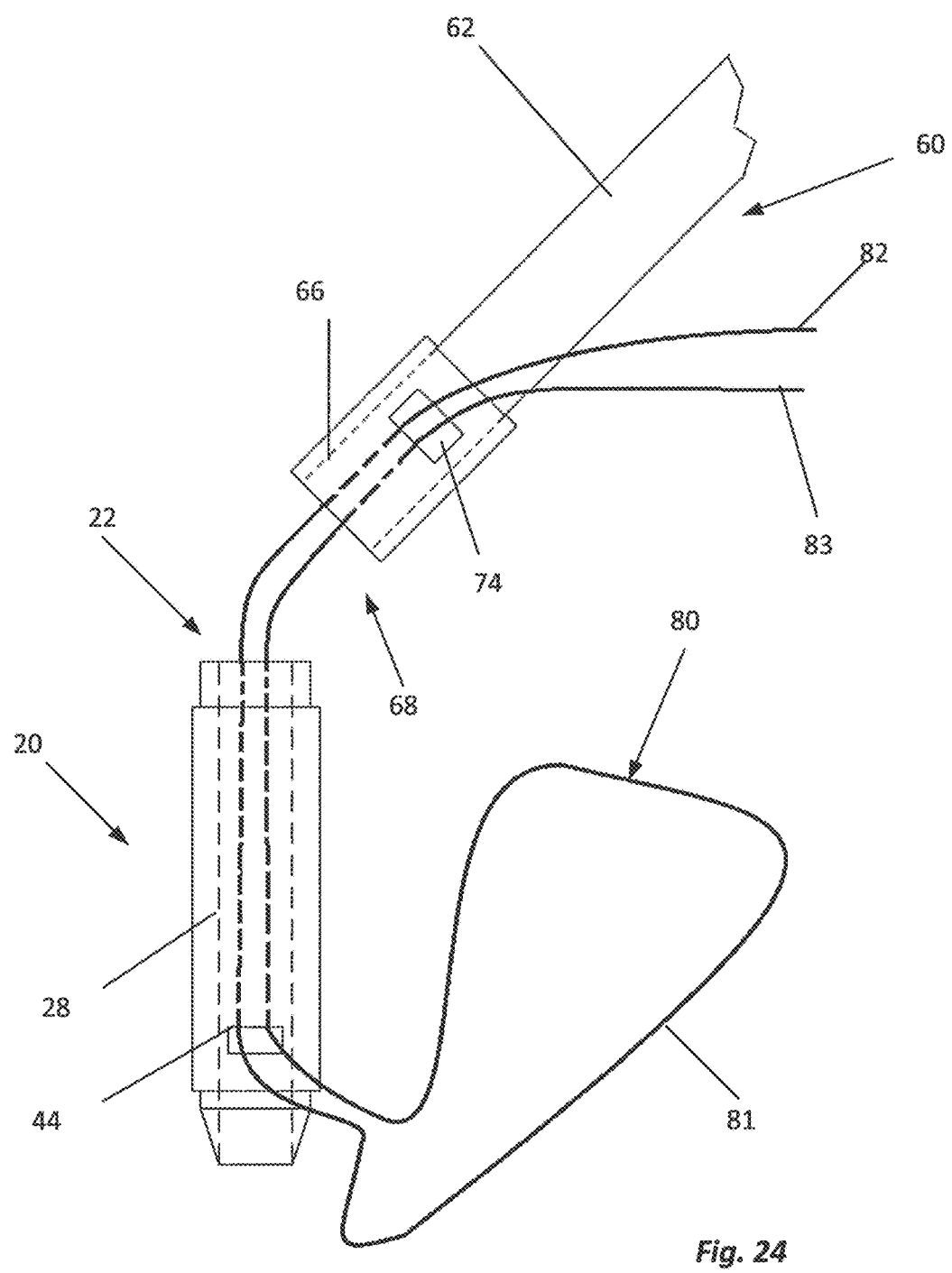
FIG. 24 shows an anchor body and insertion tool with a loop of suture material fed through the anchor body and insertion tool.

An insertion tool is illustrated in FIGS. 22-24. The insertion tool 60 includes a handle section extending from a first end of an engagement section 64. The second end 68 of the engagement section 64 is open and a second channel 66 extends from this open end to a passageway 74. Passageway 74 extends from the channel 66 through the outer surface 72. The open end 68 of the tool also has an engagement surface 70.

As illustrated in FIGS. 22 through 24, the opening in the end 68 of the engagement section 64 is large enough to receive the projection 40 of the anchor body 20. Further, end 68 of the insertion tool 60 includes an engagement surface 70 which engages the flange 38 of the suture anchor when the handle is coupled to the anchor body 20. An impaction force can then be applied using a mallet (not shown) via the handle 62 to drive the anchor body 20 into the cylindrical hole 4 in the bone. One skilled in the art will also recognize that the channel 66 of the engagement section 64 of the handle 60 and the projection 40 of the suture anchor 20 may be keyed such that rotation of the handle serves to rotate the suture anchor 20. Such keying will, of course, be advantageous and necessary when threads 52 and/or 54 are provided as opposed to ridges 50. A slightly modified insertion tool is illustrated in FIG. 21 and discussed below.

Again, the anchor body 20 shown in FIGS. 22 through 24 will typically be preloaded with suture material. FIG. 24 shows an anchor 20 which will typically be used to achieve knotless attachment of the suture material. In FIG. 23 the suture material is labeled 80. The suture material 80 includes a loop 81. The suture material 80 extends from both sides of this loop 81 such that the ends 82 and 83 of suture material 80 may be passed through the orifice 44 and channel 28 of the anchor body 20 and then out through the open top 22 of the anchor body 20. The ends 82 and 83 of the suture material 80 are then fed through (i) the opening in the end 68 of the insertion tool 60, (ii) the second channel 66 of the insertion tool 60 and back out through the passageway 74 of insertion tool 60. The free ends 82 and 83 of the suture material 80 may then be used to attach a ligament, tendon.

Figure 25:
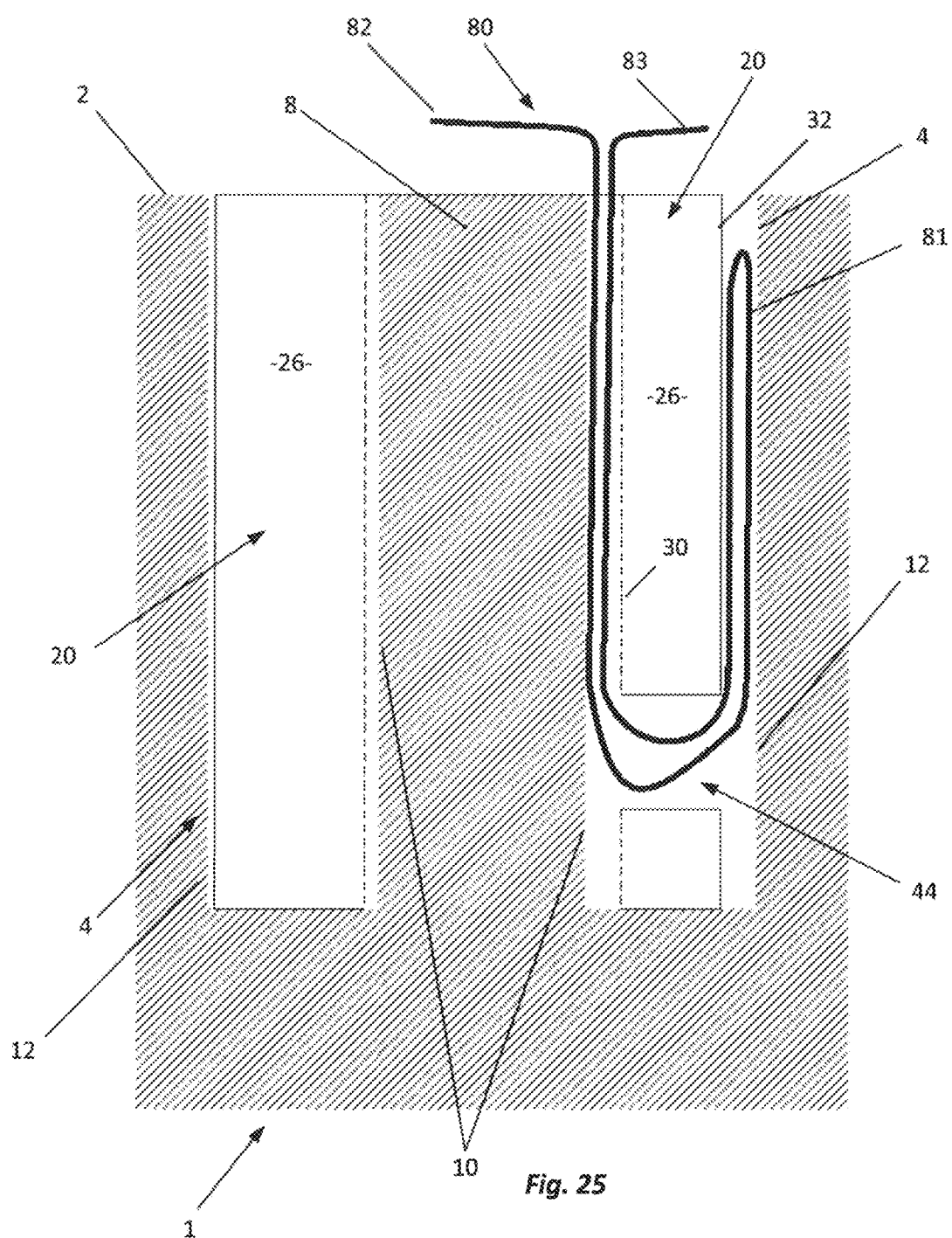
FIG. 25 shows in cross-section an anchor body positioned within a recess at an anchor point and a piece of suture material secured in place at the anchor point by the anchor body.

FIG. 25 is provided to show how the suture material 80 is held in place. As illustrated, after the insertion tool 60 has been used to force the anchor body 20 into the cylindrical hole 4, the loop 81 of the suture material resides and is pinched between the outer bone surface 12 formed by creating the cylindrical hole 4 in the bone 1 and the outer engagement surface 32 of the cylindrical wall 26 of the anchor body 20. The suture material extends from the loop 81 through the orifice 44 and into the channel 28 of the anchor body 20. Specifically, the suture material 80 extends and is pinched between the inner bone surface 10 (i.e., the surface of the bone core 8) and the inner wall 30 of the anchor body 20. The suture material 80 then extends out of the open top 22 of the anchor body 20. The free ends 82 and 83 may then be used to attach ligaments, tendons or the like to the bone, and because the portion of the suture material 80 residing within the cylindrical hole and suture anchor is so tightly pinched both between the outer bone surface 12 and the outer engagement surface 32 as well as between the inner bone surface 10 and the inner engagement surface 30, the suture material 80 is firmly coupled in place by the anchor body 20 and the bone.

Figure 18:
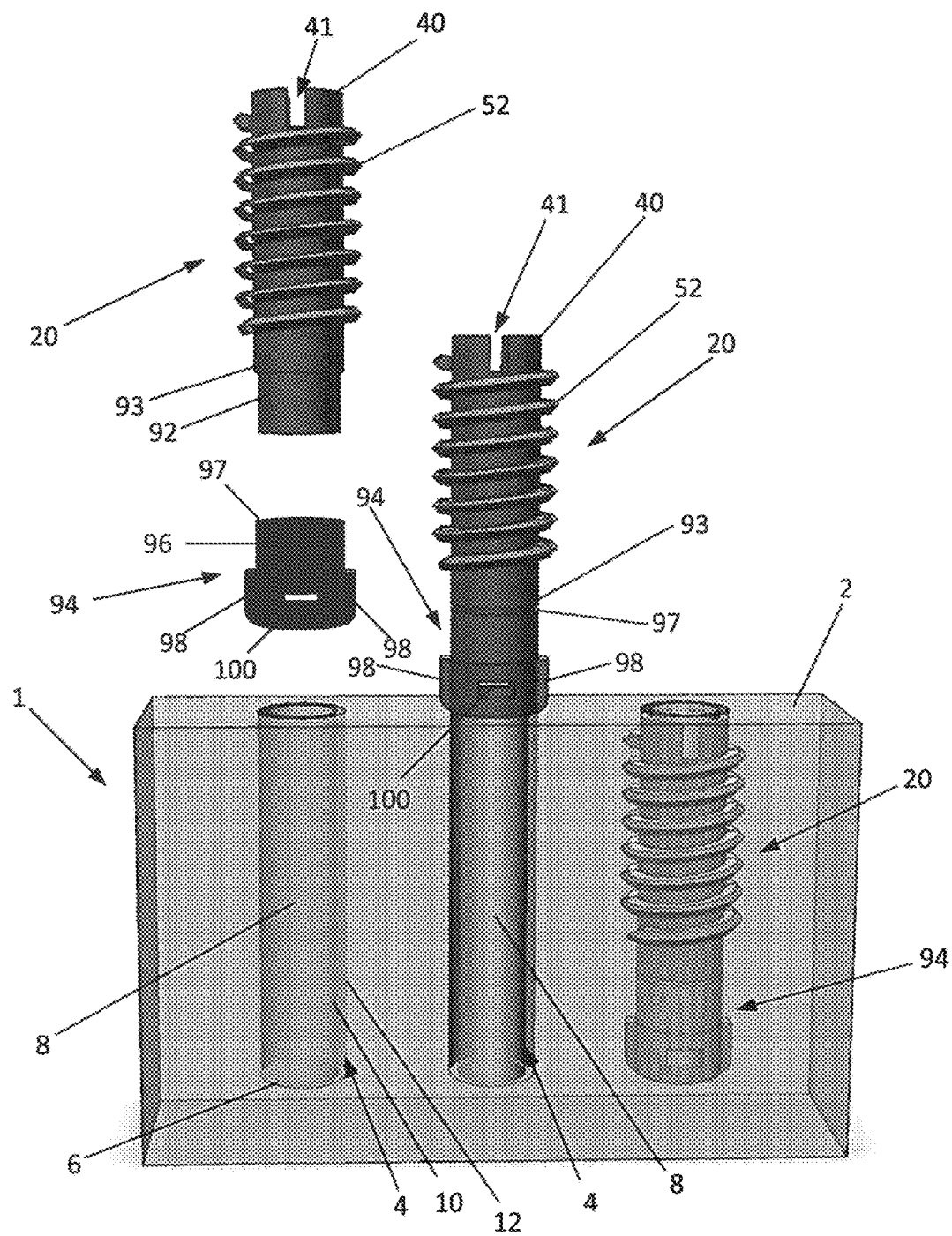
FIG. 18 is a view of a sixth embodiment of an anchor body and distal cap wherein the anchor body and cap are aligned with the recess of FIGS. 1 and 2 (left), are aligned with the recess and joined together (center) and implanted in the recess (right).

The anchor body embodiment of FIG. 18 will now be described in further detail. Anchor body 20 has, at least, external threads 52. This anchor body is, again, hollow and adapted to fit in the cylindrical hole 4 and surround a bone core 8. The external threads 50 are adapted to engage the outer bone surface 12. If inner threads such as those illustrated in FIG. 19 are provided, the inner threads 54 are adapted to engage the inner bone surface 10 (i.e., the exterior of the bone core 8) to provide even more holding power. Located at the bottom of the anchor body 20 shown in FIG. 18 is a cylindrical extension 92 projecting distally from a flange 93. Located at the proximal end of the bone anchor 20 is a proximal projection 40 having a slot 41 extending distally from the proximal end of the anchor body 20.

Also shown in FIG. 18 is a short, hollow, cylindrical cap 94 which may be loaded with suture material 80 comprising one or more suture members and positioned at the distal tip of the anchor body 20. More specifically, cap 24 has a hollow cylindrical wall 96 adapted to receive cylindrical extension 92. The cylindrical wall 96 has a proximal end 97 which engages the flange 93 when the cap 94 is coupled to the anchor body 20. The cap 94 also has a pair of outwardly extending wings 98 adapted to engage the outer bone surface 12. Like the anchor body 20, the cap is also adapted to surround the bone core 8. An orifice 100 extends through the wall 96 of the cap 94 to permit suture material 80 to be passed through the wall 96 similar to the manner shown in FIGS. 24 and 25. Prior to implantation of the anchor body 20 in the bone 1, the cap 94 is mated to the anchor body 20. The anchor body 20 and cap 94 are held together by a firm friction fit between cylindrical extension 92 and cylindrical wall 96. The assemble is then aligned with the cylindrical hole 4 and bone core 8 and pushed into the cylindrical hole 4 until the threads 52 reach the cylindrical hole 4. The anchor body 20 is then screwed into place. As the anchor body is screwed into place, the cap is driven into and secured in the bone at the distal end of the anchor body 20. Furthermore, in some embodiments the cap permits the flange of the cylindrical extension 92 of anchor body 20 to rotate freely within the cap 94, without necessarily generation rotation of the cap itself. Thus, the cap 94 is driven deeper into the prepared recess without rotating.

Various tools may be used to implant the anchor body 20 and cap 94 shown in FIG. 18. One such tool 60 is shown in FIG. 21. This tool is nearly identical to the impaction tool 60 shown in FIGS. 22 through 24. The sole difference is that a plate 69 has been added which extends across the second end 68 of the engagement section. This plate is adapted to be received within the slot 41 of the anchor body 20 shown in FIG. 18. This allows the tool first to be used to impact the anchor body 20 and cap 94 into the cylindrical hole 4 until the threads 52 engage the cylindrical hole, and then to be used to rotate the anchor body 20 to drive the anchor body 20 and cap 94 into their final implanted position within the cylindrical hole 4 and surrounding the bone core 8. Other tools, such as an ordinary screw driver, could also be fitted in the slot 41 to perform these functions. However, the tool 60 illustrated in FIG. 21 offers better control. Also, the cylindrical wall 66 is adapted to frictionally engage the projection 40 to temporarily hold the tool 60 to the anchor body 20 in a similar manner to the way the cap 94 is frictionally held to the cylindrical extension 92. Thus, during implantation, the surgeon is able to hold, with one hand and in assembled relation, the entire assembly comprising the anchor body 20, cap 94, suture material 80 and tool 60.

Implantation of the anchor body 20 may also be simplified by providing the distal tip of the anchor body (e.g., 24 in FIG. 3) or a distal cap (e.g., 94 in FIG. 18) associated therewith which is reinforced with or formed of a sharpened ring of metal alloy that permits the anchor body (or cap) to form its own recess as it is being impacted into the recipient bone. This eliminates the need for prior formation of the recess. In such embodiments, the anchor body would be considered "self-punching" as it would form its own recess.

The foregoing description is intended to explain the various features and advantages, but is not intended to be limiting. The scope of the invention is defined by the following claims which are also intended to cover a reasonable range of equivalents.

What is claimed is:

1. A suture anchor designed to be secure within a recess prepared in bone, said recess (i) extending inwardly from an exposed surface of the bone, (ii) comprising a cylindrical hole extending inwardly from the exposed surface to a base and surrounding a bone core extending from the base toward the exposed surface of the bone, and (iii) defining an inner bone surface and an outer bone surface, said suture anchor comprising: an anchor body having a fixed open top, a fixed open bottom, a cylindrical wall generally extending from the fixed open top to the fixed open bottom and defining an inner engagement surface surrounding a channel and an outer engagement surface, the outer engagement surface engages the outer bone surface of the recess and the inner engagement surface engages the inner bone surface;

wherein the anchor body is configured to be disposed within the recess such that the fixed open bottom is advanced toward the base of the recess; and wherein the suture anchor is configured to permit at least a portion of the cylindrical wall to be inserted into the cylindrical hole of the recess such that the bone core resides in the channel.

2. The suture anchor of claim 1 further comprising at least one orifice extending through the cylindrical wall between the inner engagement surface and the outer engagement surface.

3. The suture anchor of claim 1 wherein the cylindrical wall has a flange adapted to engage an insertion tool coupled to the suture anchor.

4. The suture anchor of claim 1 wherein said outer engagement surface includes a plurality of ridges.

5. The suture anchor of claim 1 wherein said inner engagement surface includes a plurality of ridges.

6. The suture anchor of claim 1 wherein said outer engagement surface and said inner engagement surface each include a plurality of ridges.

7. The suture anchor of claim 1 wherein said outer engagement surface includes threads.

8. The suture anchor of claim 1 wherein said inner engagement surface includes threads.

9. The suture anchor of claim 1 wherein said inner engagement surface and said outer engagement surface each include threads.

10. The suture anchor of claim 1 further including suture material coupled to the bone by the anchor body.

11. The suture anchor of claim 1, wherein the anchor body comprises vents through the cylindrical walls.

12. The suture anchor of claim 1, wherein the anchor body comprises a pair of first orifices that are axially aligned and extend through the cylindrical wall between the inner engagement surface and the outer engagement surface.

13. The suture anchor of claim 12, wherein the cylindrical wall has a recess that extends upwardly from each of the first orifices.

14. The suture anchor of claim 12, wherein each of the first orifices is configured to receive suture material through the cylindrical wall.

15. The suture anchor of claim 1, wherein the anchor body comprises a bottom portion that is proximate the open bottom, and wherein the bottom portion includes a tapered section.

16. The suture anchor of claim 1, wherein the anchor body comprises a top portion that is proximate the open top, and wherein the top portion includes a flange surrounding a narrowed projecting portion.

17. The suture anchor of claim 16, wherein the flange surrounding the narrowed projecting portion is configured to couple with an insertion tool.

18. The suture anchor of claim 1, wherein a proximal end of the anchor body forms the open top, and wherein the proximal end comprises a projection having a slot extending distally from the proximal end of the anchor body.

19. The suture anchor of claim 18, wherein the slot is configured to receive a screwdriver.

20. A suture anchor designed to be secure within a recess prepared in bone, said recess (i) extending inwardly from an exposed surface of the bone, (ii) comprising a cylindrical hole extending inwardly from the exposed surface to a base and surrounding a bone core extending from the base toward the exposed surface of the bone, and (iii) defining an inner bone surface and an outer bone surface, said suture anchor comprising: an anchor body having an open top, an open bottom, a cylindrical wall generally extending from the open top to the open bottom and defining an inner engagement surface surrounding a channel and an outer engagement surface, wherein the suture anchor body is adapted to permit at least a portion of the cylindrical wall to be inserted into the cylindrical hole of the recess such that the bone core resides in the channel, the outer engagement surface engages the outer bone surface of the recess and the inner engagement surface engages the inner bone surface, wherein said anchor body has a cylindrical extension projecting distally from a flange, and said suture anchor further comprised hollow cylindrical cap adapted to be loaded with suture material and adapted to receive the cylindrical extension, said cap having a proximal end which engages the flange when the cap is coupled to the anchor body.

* * * * *